(12) United States Patent
Bacon et al.

(10) Patent No.: US 8,395,012 B2
(45) Date of Patent: Mar. 12, 2013

(54) DISPOSABLE ABSORBENT ARTICLES CONTAINING ODOR CONTROLLING FILMS

(75) Inventors: Dennis Ray Bacon, Cincinnati, OH (US); Matthew Joel Taylor, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 586 days.

(21) Appl. No.: 11/716,149

(22) Filed: Mar. 9, 2007

(65) Prior Publication Data

US 2007/0213412 A1  Sep. 13, 2007

Related U.S. Application Data

(60) Provisional application No. 60/781,240, filed on Mar. 10, 2006.

(51) Int. Cl.
*A61F 13/15* (2006.01)
*C09K 3/00* (2006.01)

(52) U.S. Cl. ........... 604/359; 604/358; 516/53; 514/938

(58) Field of Classification Search ................... 604/317, 604/359; 516/53; 514/938
See application file for complete search history.

(56) References Cited

U.S. PATENT DOCUMENTS

| | | | |
|---|---|---|---|
| 3,565,243 A | 2/1971 | Freeman | |
| 3,852,475 A * | 12/1974 | Tarangul | 514/778 |
| 3,860,003 A | 1/1975 | Buell | |
| 3,911,173 A | 10/1975 | Sprague, Jr. | |
| 3,929,135 A | 12/1975 | Thompson | |
| 3,971,852 A * | 7/1976 | Brenner et al. | 426/103 |
| 4,324,246 A | 4/1982 | Mullane et al. | |
| 4,342,314 A | 8/1982 | Radel et al. | |
| 4,463,045 A | 7/1984 | Ahr et al. | |
| 4,554,297 A | 11/1985 | Dabi | |
| 4,609,518 A | 9/1986 | Curro et al. | |
| 4,610,678 A | 9/1986 | Weisman et al. | |
| 4,629,643 A | 12/1986 | Curro et al. | |
| 4,636,207 A | 1/1987 | Buell | |
| 4,673,402 A | 6/1987 | Weisman et al. | |
| 4,695,278 A | 9/1987 | Lawson | |
| 4,704,115 A | 11/1987 | Buell | |
| 4,740,520 A | 4/1988 | Hallenbach et al. | |
| 4,785,996 A | 11/1988 | Ziecker et al. | |
| 4,795,454 A | 1/1989 | Dragoo | |
| 4,834,735 A | 5/1989 | Alemany et al. | |
| 4,842,666 A | 6/1989 | Werenicz | |
| 4,888,231 A | 12/1989 | Angstadt | |
| 4,892,536 A | 1/1990 | Desmarais et al. | |
| 4,900,317 A | 2/1990 | Buell | |
| 4,909,803 A | 3/1990 | Aziz et al. | |
| 4,940,464 A | 7/1990 | Van Gompel et al. | |
| 4,950,254 A | 8/1990 | Andersen et al. | |
| 4,988,344 A | 1/1991 | Reising et al. | |
| 4,988,345 A | 1/1991 | Reising | |
| 4,990,147 A | 2/1991 | Freeland | |
| 5,006,394 A | 4/1991 | Baird | |
| 5,037,416 A | 8/1991 | Allen et al. | |
| 5,085,654 A | 2/1992 | Buell | |
| 5,092,861 A | 3/1992 | Nomura et al. | |
| 5,112,688 A | 5/1992 | Michael | |
| 5,147,345 A | 9/1992 | Young et al. | |
| 5,151,092 A | 9/1992 | Buell et al. | |
| B14842666 I5 | 10/1992 | Werenicz | |
| 5,221,274 A | 6/1993 | Buell et al. | |
| 5,234,423 A | 8/1993 | Alemany et al. | |
| 5,246,433 A | 9/1993 | Hasse et al. | |
| 5,260,345 A | 11/1993 | Desmarais et al. | |
| 5,269,775 A | 12/1993 | Freeland et al. | |
| 5,324,444 A | 6/1994 | Berry et al. | |
| 5,342,338 A | 8/1994 | Roe | |
| 5,393,527 A * | 2/1995 | Malick et al. | 435/7.1 |
| RE34,920 E | 4/1995 | Aziz et al. | |
| 5,492,751 A | 2/1996 | Butt, Sr. et al. | |
| 5,500,138 A | 3/1996 | Bacon et al. | |
| 5,507,760 A | 4/1996 | Wynne et al. | |
| 5,554,145 A | 9/1996 | Roe et al. | |
| 5,562,646 A | 10/1996 | Goldman et al. | |
| 5,569,234 A | 10/1996 | Buell et al. | |
| 5,580,411 A | 12/1996 | Nease et al. | |
| H1630 H | 1/1997 | Roe et al. | |

(Continued)

FOREIGN PATENT DOCUMENTS

| | | |
|---|---|---|
| EP | 0 550 067 A1 | 7/1993 |
| JP | 02-291865 A | 12/1990 |

(Continued)

OTHER PUBLICATIONS

J. Chem. Inf. Comp. Sci. 271, 21 (1987).

(Continued)

*Primary Examiner* — Susan Su
(74) *Attorney, Agent, or Firm* — Abbey A. Lopez; Amy M. Foust

(57) ABSTRACT

Stable odor controlling compositions, methods for incorporating the compositions, and disposable absorbent articles, which release perfume and subsequently are able to minimize odor caused from bodily fluids via the presence of an oil-in-water emulsion that serves as a carrier and preservation system for the perfume. The stable odor controlling emulsion compositions include an oil-in-water emulsion comprising: a) an aqueous phase comprising a modified starch and water; b) an oil phase comprising a perfume; c) an effective amount of a rheology modifier; d) an effective amount of a co-surfactant; and e) an effective amount of an antimicrobial agent; wherein said emulsion composition is applied to said article in the form of stable emulsion droplets having an median size of less than about 1 μm and dries to form a discontinuous film.

13 Claims, No Drawings

U.S. PATENT DOCUMENTS

| | | | |
|---|---|---|---|
| 5,599,335 A | 2/1997 | Goldman et al. | |
| 5,607,760 A | 3/1997 | Roe | |
| 5,609,587 A | 3/1997 | Roe | |
| 5,628,097 A | 5/1997 | Benson et al. | |
| 5,635,191 A | 6/1997 | Roe et al. | |
| H1670 H | 7/1997 | Aziz et al. | |
| 5,643,588 A | 7/1997 | Roe et al. | |
| 5,769,838 A | 6/1998 | Buell et al. | |
| 5,858,959 A * | 1/1999 | Surutzidis et al. | 510/507 |
| 5,865,824 A * | 2/1999 | Chen et al. | 604/378 |
| 5,897,545 A | 4/1999 | Kline et al. | |
| 5,899,895 A | 5/1999 | Robles et al. | |
| 5,899,896 A | 5/1999 | Suprise et al. | |
| 5,916,661 A | 6/1999 | Benson et al. | |
| 5,935,826 A | 8/1999 | Blue et al. | |
| 5,941,864 A | 8/1999 | Roe | |
| 5,957,908 A | 9/1999 | Kline et al. | |
| 5,968,025 A | 10/1999 | Roe et al. | |
| 6,004,306 A | 12/1999 | Robles et al. | |
| 6,086,917 A | 7/2000 | Trubiano et al. | |
| 6,087,322 A * | 7/2000 | Morelli et al. | 512/25 |
| 6,107,539 A | 8/2000 | Palumbo et al. | |
| 6,118,041 A | 9/2000 | Roe et al. | |
| 6,120,487 A | 9/2000 | Ashton | |
| 6,120,489 A | 9/2000 | Johnson et al. | |
| 6,194,362 B1 | 2/2001 | Trinh et al. | |
| 6,217,890 B1 * | 4/2001 | Paul et al. | 424/402 |
| 6,414,215 B1 | 7/2002 | Roe | |
| 6,450,997 B1 * | 9/2002 | Seitz et al. | 604/385.01 |
| 6,476,288 B1 | 11/2002 | Vanrijswijck et al. | |
| 6,545,197 B1 | 4/2003 | Muller et al. | |
| 6,608,017 B1 * | 8/2003 | Dihora et al. | 510/349 |
| 6,627,787 B1 | 9/2003 | Roe et al. | |
| 6,663,306 B2 * | 12/2003 | Policicchio et al. | 401/138 |
| 6,680,422 B2 | 1/2004 | Roe | |
| 6,790,798 B1 | 9/2004 | Suzuki et al. | |
| 6,835,377 B2 | 12/2004 | Goldberg et al. | |
| 7,053,034 B2 * | 5/2006 | Shefer et al. | 510/349 |
| 2002/0017376 A1 | 2/2002 | Geltser et al. | |
| 2003/0233082 A1 | 12/2003 | Kline et al. | |
| 2004/0097895 A1 | 5/2004 | Busam et al. | |
| 2004/0158212 A1 | 8/2004 | Ponomarenko et al. | |
| 2004/0158213 A1 | 8/2004 | Ponomarenko et al. | |
| 2004/0158214 A1 | 8/2004 | Ponomarenko et al. | |
| 2004/0241333 A1 | 12/2004 | Cielenski et al. | |
| 2005/0256476 A1 * | 11/2005 | Mirle et al. | 604/382 |
| 2006/0039934 A1 * | 2/2006 | Ness et al. | 424/401 |
| 2007/0128722 A1 | 6/2007 | Lin et al. | |
| 2008/0200894 A1 * | 8/2008 | Gatto et al. | 604/385.01 |
| 2009/0000979 A1 * | 1/2009 | Woo et al. | 206/524.6 |

FOREIGN PATENT DOCUMENTS

| | | |
|---|---|---|
| JP | 03-080867 A | 4/1991 |
| WO | WO 94 22501 A1 | 10/1994 |
| WO | WO-9524173 A3 | 10/1995 |
| WO | WO 98/26808 A2 | 6/1998 |
| WO | WO 98/51317 A1 | 11/1998 |
| WO | WO-99/55819 | 11/1999 |
| WO | WO 99/65458 | 12/1999 |
| WO | WO-0069382 A1 | 11/2000 |
| WO | WO 01/05926 | 1/2001 |
| WO | WO 01/60299 A1 | 8/2001 |
| WO | WO 2004/108177 A1 | 12/2004 |

OTHER PUBLICATIONS

J. Chem. Inf. Comp. Sci. 29, 163 (1989).

International Search Report, PCT/US2007/006088, mailed Oct. 10, 2007.

International Search Report, PCT/US07/006088, mailed Oct. 15, 2008.

* cited by examiner

DISPOSABLE ABSORBENT ARTICLES CONTAINING ODOR CONTROLLING FILMS

CROSS REFERENCE TO RELATED APPLICATION

This application claims the benefit of U.S. Provisional Application No. 60/781,240, filed Mar. 10, 2006.

FIELD OF INVENTION

The present disclosure generally relates to films, oil-in-water compositions, methods for incorporating such compositions/films into disposable absorbent article, and such disposable absorbent articles, all in which a perfume is released and subsequently minimizes odor caused from bodily fluids via the presence of a film formed from a stable oil-in-water emulsion composition that serves as a carrier and preservation system for the perfume.

BACKGROUND OF THE INVENTION

A wide variety of fluid absorbent structures known in the art are useful for absorbing body fluids such as blood, urine, and menses. Ideally, these products should be sanitary and comfortable in use. Disposable absorbent products of this type generally comprise a fluid-permeable topsheet material, a fluid absorbent core, and a backsheet material. Various shapes, sizes and thicknesses of such articles have been explored in an attempt to make their use more comfortable and convenient.

Odor control and odor masking in disposable absorbent products has been researched from a number of different perspectives over the years to alleviate the discomfort that accompanies unpleasant odors during use of such products. Additionally, such products, after use, often develop an especially unpleasant odor and require special handling and disposal to mitigate and contain the unpleasant odor. For instance, many bodily fluids have an unpleasant odor, or develop such odors when in contact with air and/or bacteria for prolonged periods. Consumers typically use malodor to determine the need for change of a diaper, catamenial and the like. For example, malodor is also an integral component of the toilet training process for both caregiver and infant wearer.

One alternative to relying on body malodor as one factor to indicate the need to change the disposable absorbent product is through the use of a "scent signal." A "scent signal" is a positive perfume odor which signals to a consumer the need to at least inspect, if not remove the absorbent product. Alternatively, the scent signal may merely work to neutralize or mask the malodor caused when bodily exudates contact the atmosphere in such a way that others are not offended by the smell of the wetted product. Typically, the scent signal is released when contacted by bodily fluids, such as sweat, urine, menses and the like.

One material which is suitable for incorporation into absorbent products to generate a scent signal are the starch encapsulated perfume accords, or SEA. SEAs are generally solid particles comprising water-soluble cellular matrixes containing perfume stably held in the cells. Encapsulating specific ingredients in a starch-based encapsulate is well known where it is desired to form a water-soluble barrier between the component ingredients and its environment. The encapsulation is usually to protect a sensitive ingredient from its environment, or vice versa. When SEAs are contacted with water, such as moisture, urine, menses, etc, or exposed to high water vapor content gas (relative humidity), the water-soluble cellular matrix at least partially dissolves or is plasticized thereby allowing for the perfumes release, thereby generating a scent signal.

In addition, for perfumes there is an additional factor that consumers do not like to be overwhelmed by strong perfume odors on opening a bag or other container of diapers or absorbent product. In order to provide sufficient odor fragrance scent, when wet, a relatively high amount of perfume is needed. However, high levels of perfume tend to make unacceptably strong odor for the dry, unused, diaper or absorbent product itself. Encapsulation was therefore developed as a way of introducing more perfume into a product where it is desired that the product itself should not have a very strong odor when dry, and generate a scent signal, when wet.

The manufacture of starch particle encapsulates is related to the production of fine particulate material during manufacture. Since these materials are flammable, a build up of very fine particles may be explosive in the presence of oxygen and a source of ignition such as a spark. Though it would be advantageous to incorporate SEA particle encapsulates into absorbent products to provide a scent signal, there are numerous problems associated with their manufacture. An area of improvement for adding SEAs particles to an absorbent product, generally relates to the need for accuracy in the incorporation of SEA particles onto a substrate. For instance, it is difficult and costly to be able to deliver SEA particles to a substrate with any degree of reasonable accuracy required for a commercial process. Typically, these problems are related to preventing or minimizing the SEAs exposure to moisture and reducing and/or eliminating the potential for the SEAs particles to generate dust during manufacture and during incorporation into the absorbent product. For instance, they require a carrier media that permits storage and facilitates transport to the intended surface in the absorbent product. Typically, this carrier requires heating and mixing prior to application of the SEA to the substrate's surface. A proposed solution to these processing problems is detailed in US Patent Publication 2004/0241333 A1 (Cielenski et al.) published on Dec. 2, 2004.

Applicants have determined that it would be just as advantageous to provide a perfume, in an oil-in-water emulsion composition comprising a water soluble encapsulant, which is a modified starch, that is able to retain its stability over extended period of times without the need for additional mixing, blending, or heating immediately prior to application of the composition to a substrate surface. Ideally, this mode of manufacture will afford flexibility to yield either 1) a negligible level of 'surface free perfume oil' upon dehydration or 2) some 'free perfume oil' upon dehydration of the oil-in-water emulsion. A negligible level of amount of "surface free oil" will minimize perfume lost to evaporation, such that the overall manufacturing process becomes more efficient and the end user realizes the full benefit of the perfume as delivered to the disposable absorbent article when released and made wet. Having some amount of 'surface free oil', upon dehydration of the emulsion, affords the opportunity to connote fragrance odor to the dry product, separate and in addition to fragrance expressed, upon wetting of the dehydrated oil-in-water emulsion, if necessary to mask and offset other odors associated with the absorbent article's manufacture, e.g, adhesives.

SUMMARY OF THE INVENTION

According to one aspect of the present disclosure, a disposable absorbent article includes an odor controlling film formed from a stable oil-in-water emulsion composition comprising: a) an aqueous phase comprising a modified starch and water; b) an oil phase comprising a perfume; c) an effective amount of a rheology modifier; d) an effective amount of a co-surfactant; and e) an effective amount of an antimicrobial agent; wherein said emulsion composition is applied to said article in the form of stable emulsion droplets having a median size of less than about 1 μm and dries to form the odor controlling film.

DETAILED DESCRIPTION OF THE INVENTION

As used herein, the term "comprising" means that the various components, ingredients, or steps, can be conjointly employed in practicing embodiments according to the present disclosure. Accordingly, the term "comprising" is open-ended and encompasses the more restrictive terms "consisting essentially of" and "consisting of." Other terms may be defined as they are discussed in greater detail herein.

The process according to the present disclosure comprises the steps of providing, delivering and applying an effective amount of an odor controlling film via a stable oil-in-water emulsion composition to a disposable absorbent article.

Odor Controlling Emulsion Composition

According to one embodiment, the odor controlling film is formed from a stable oil-in-water emulsion composition that further comprises an aqueous phase comprising a modified starch and water, an oil phase comprising a perfume, an effective amount of a rheology modifier, an effective amount of a co-surfactant (as the starch has some emulsification properties), and an effective amount of an antimicrobial agent.

Desirably, at least an effective amount of the oil-in-water emulsion composition is applied to the article such that the resultant film comprises the requisite amount of perfume for release upon wetting. Effective amounts are typically those which provide either a noticeable scent signal to the consumer to signify to the caregiver/wearer that the substrate on which the emulsion composition is disposed has been contacted with sufficient aqueous fluid (e.g., menses, urine, etc.) or water containing solid (e.g., feces) or exposed to a high water vapor content gas (relative humidity), or provide a noticeable masking effect to those around the user of the disposable absorbent product such that the wetting of the product goes unnoticed. For instance, in one embodiment the emulsion composition is disposed or applied to a substrate that is incorporated into a disposable absorbent article. In such a case, the typical amount of the emulsion composition present on the substrate is from about 0.001 g, 0.005 g, or 0.01 g to about 0.5 g, 1 g, or 5 g, per substrate.

According to one group of embodiments, the aqueous phase of the emulsion composition comprises from about 35%, 38%, 40%, or even 42% to about 45%, 50%, 55%, 60%, 65%, 70%, 75%, 80%, 85%, 90%, or even to about 90% water, by weight of the composition. The oil-in-water emulsion is prepared by merely mixing the various components of the composition together. Typically, however, the starch and water are mixed initially and the remaining constituents are added to the mixture all at once or sequentially.

The modified starch in the aqueous phase is present in an amount of from about 7.5%, 10%, 15%, 20% to about 25%, 30%, 35%, 40%, or even about 45%. Modified starches suitable for use in this first step can be made from raw starch, pregelatinized starch, modified starch derived from tubers, legumes, cereal and grains, for example, corn starch, wheat starch, rice starch, waxy corn starch, oat starch, cassava starch, waxy barley starch, waxy rice starch, sweet rice starch, amioca, potato starch, tapioca starch and mixtures thereof.

Suitable modified starches include hydrolyzed starch, hydrogenated starch hydrolysates, acid thinned starch, starch having hydrophobic groups, such as starch esters of long chain hydrocarbons (C5 or greater), starch acetates, starch octenyl succinate and mixtures thereof. In one embodiment, hydrogenated starch hydrolysates of narrow polydispersity, and starch esters, particularly starch octenyl succinates, and mixtures thereof, are preferred.

The term "hydrolyzed starch" refers to oligosaccharide-type materials that are typically obtained by acid and/or enzymatic hydrolysis of starches, preferably corn starch. In one embodiment, these hydrolyzed starch maltodextrins have Dextrose Equivalent (DE) values of from about 10 to about 50, in another embodiment from about 15 to about 30, or in yet another embodiment from about 17 to about 23 DE. According to certain examples, the starch hydrolysates of narrow DE polydispersity are preferred. According to other examples, hydrogenated starch hydrolysates of narrow DE polydispersity are preferred. The DE value is a measure of the reducing equivalence of the hydrolyzed starch referenced to dextrose and expressed as a percent (on a dry basis). The higher the DE value, the more reducing sugars present. A method for determining DE values can be found in Standard Analytical Methods of the Member Companies of Corn Industries Research Foundation, 6th ed. Corn Refineries Association, Inc. Washington, D.C. 1980, D-52.

Exemplary modified starch hydrolyslates are LAB 9088 and LA B9090 which are commercially available from Rouquette America Inc.

It may be preferred to include in the starch water-mixture, a starch ester. According to one embodiment, the hydrolyzed starches, particularly for starch ester or mixture of starch esters, have Dextrose Equivalent (DE) values of from about 20 to about 80, in another embodiment from about 20 to about 50, or in yet another embodiment from about 25 to about 38 DE. Well suited modified starches are those wherein the starch is gelatinized and the hydrophobic group comprises an alkyl, or an alkenyl group which contains at least five carbon atoms or an aralkyl or aralkenyl group which contains at least six carbon atoms. Starches for use in accordance with the present disclosure are starch esters. These will typically have a degree of substitution in the range of from about 0.01% to about 10%. The hydrocarbon part of the modifying ester should preferably be a $C_5$ to a $C_{16}$ carbon chain. As stated above, in one embodiment octenyl succinate is the preferred ester. Preferably, octenyl succinate (OSAN) substituted waxy corn starches of various types such as 1) waxy starch, acid thinned and OSAN substituted, (2) blend of corn syrup solids: waxy starch, OSAN substituted and dextrinized, 3) waxy starch: OSAN substituted and dextrinized, 4) blend of corn syrup solids or maltodextrins with waxy starch: acid thinned OSAN substituted then cooked and spray dried, 5) waxy starch: acid thinned OSAN substituted then cooked and spray dried; and 6) the high and low viscosities of the above modifications (based on the level of acid treatment) can also be used in the present disclosure. Mixtures of these, particularly mixtures of the high and low viscosity modified starches are also suitable.

The aqueous starch mixture may also include a plasticizer for the starch. Suitable examples include monosaccharides, disaccharides, oligosaccharides, maltodextrins, such as glucose, maltose, sucrose, maltodextrins of DE greater than 30, glycerol and sorbitol.

An exemplary modified starch is HICAP 100 which is commercially available from National Starch & Chemical.

According to the present disclosure, suitable modified starches are those comprising a starch derivative containing a hydrophobic group or both a hydrophobic and a hydrophilic group which has been degraded by at least one enzyme capable of cleaving the 1,4 linkages of the starch molecule from the non-reducing ends to produce short chained saccharides to provide high oxidation resistance while maintaining substantially high molecular weight portions of the starch base. Such starches are described in U.S. Pat. Nos. 5,935,826 and 6,086,917, both assigned to National Starch & Chemical Investment Holding Corporation.

Exemplary modified starches include National LNP GLUK 2004 and HICAP 100, which are commercially available from National Starch & Chemical.

Without being limited by theory, it is believed that the functional modifications of the starch materials of the present disclosure provide emulsification properties to the mixture of materials of the composition.

The emulsion composition further comprises an effective amount of a rheology modifier. In one embodiment, rheology modifying agents possessing pseudoplastic behavior are preferred. Pseudoplastic materials are characterized by viscosity which increases and decreases virtually instantaneously in response to the removal and application of shear. This property results in fluids which readily flow, and facilitate a spray add-on or coating process but are capable of suspending or stabilizing components. Suitable modifiers include, but are not limited to, polysaccharides maltodextrins, natural gums, and modified starches, such as Xanthan gum, Gellan gum, Diutan gum, Welan gum, Gum Arabic, Guar gum, maltodextrins, hydroxylpropyl distarch phosphate, starch octenyl succinae (undegraded). According to certain embodiments, the rheology modifier, or combinations thereof, is present in an effective amount of from about 0.02%, 0.05%, 0.1% to about 0.3%, 0.4%, or 0.5%, by weight of the composition.

The oil phase of the emulsion composition comprises a perfume. The perfume may comprise components that are moderately to strongly hydrophobic. In one embodiment, the perfume maximally contains less than 15% by weight of non-perfume hydrophilic solvents, typified as having an octanol-water partition coefficient (P)<1 and composed of at least 5 different component ingredients, moderately to strongly hydrophobic components, defined as having low water solubility and an octanol-water partition coefficient (P)>1. The perfume may include highly volatile, low boiling ingredients or low volatility, high boiling ingredients or even a combination of such ingredients. These highly volatile perfume ingredients are fleeting and are quickly lost as they are released. The highly volatile perfume ingredients are those having boiling points less than 250° C. Many of the more moderately volatile perfume ingredients are also quickly lost. The moderately volatile perfume ingredients are those having boiling points of greater than 250° C. to about 300° C. Exemplary perfumes include those similar to Q31535 supplied by Quest International BV. According to certain embodiments, the perfume is present in an amount of from about 5%, 8%, 10%, 15% to about 20%, 25%, 20, or 35%, by weight of the composition.

These ingredients are conventional and well known in the art. Selection of any perfume component, or amount of perfume, is based on functional and aesthetic considerations. The octanol/water partition coefficient (P) is a measure of the ratio of the concentrations of a particular solvent or perfume ingredient in octanol and water at equilibrium. The partition coefficients are conveniently expressed and reported as their logarithm to the base 10; logP. The logP of several solvent and perfume ingredient species has been reported; for example, the Ponmona92 database, available from Daylight Chemical Information Systems, Inc. (Daylight CIS), contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ransden, Eds., p. 295, Pergamon Press, 1990, incorporated herein by reference). The fragment approach is based on the chemical structure of each HR species, and takes into account the numbers and types of atoms, the atom connectivity, and chemical bonding. ClogP values are the most reliable and widely used estimates for octanol water partitioning. It will be understood by those skilled in the art that experimental log P values could also be used. Experimental log P values represent a less preferred embodiment of the invention. Where experimental log P values are used, the one hour log P values are preferred. Other methods that can be used to compute ClogP include, e.g., Crippen's fragmentation method as disclosed in J. Chem. Inf. Comput. Sci., 27a,21 (1987); Viswanadhan's fragmentation method as disclosed in J. Chem. Inf. Comput. Sci., 29, 163 (1989); and Broto's method as disclosed in Eur. J. Med. Chem.—Chim. Theor., 19, 71 (1984).

Additionally, perfumes may be selected based on their appropriateness for the intended use based on the methods detailed in U.S. Pat. No. 5,500,138 as a residual fragrance, i.e., a diaper or absorbent product that slowly releases fragrances and last for a long time, and U.S. Pat. No. 6,194,362 as a blooming fragrance, i.e., a diaper or absorbent product that releases fragrances quickly upon wetting.

The emulsion compositions of the present disclosure further comprise an effective amount of a co-surfactant. Without being limited by theory, it is believed that when this co-surfactant and the abovementioned rheology modifier are paired with the appropriate shearing mechanism that reduces the median droplet size of the overall composition to less than about 1 µm (or even less than about 0.8 µm or 0.7 µm), the compositions are able to remain stable for extended periods of time in storage prior to use. In one embodiment, prior to mixing a premix or preblend of the co-surfactant and rheology modifier is prepared. This ability to store the emulsion compositions for extended periods of times facilitates the manufacturing process where the compositions are applied to a substrate because the heightened stability does away with the need to re-emulsify the composition after storing and prior to application to the substrate. Otherwise, a mixer is required directly on the manufacturing line to re-blend the emulsion to ensure that the desired droplet size is achieved prior to application of the composition to the substrate.

Typically, the co-surfactant is present in an amount that is effective to emulsify the given amount of co-constituents within the emulsion composition. The co-surfactant may be a portion or component of the oil phase of the emulsion composition. The co-surfactant of the present invention exhibits an HLB of from about 8 to about 10 or preferably about 9. Suitable co-surfactants may be selected from the group consisting of nonionic surfactants. In particular, sorbitan fatty esters, glycerol fatty esters—mono and di glyceride, ethoxylated sorbitan fatty esters, and combinations thereof would be suitable. Exemplary cosurfactants include those similar to PGE 2-1-P (distilled diglycerol monopalmitate) supplied by Dansico, polyoxyethelene(5) sorbitan monooleate (Lonzest SMO-5) supplied by Lonza Inc., and more preferred, sorbitan monolaurate (Glycomul L), supplied by Lonza Inc.

The emulsion composition of the present invention additionally comprises an effective amount of an antimicrobial agent. Without being limited by theory, it is believed that an effective amount of a suitable antimicrobial agent will be that amount that aids in the enduring stability of the emulsion composition and prevent the deleterious degradation of the composition by bacteria. Suitable antimicrobial agents include methylchloroisothiazolinone and methylisothiazolinone, which are commercially available from Rohm & Haas under the names Kathon CG and Kathon CG II, respectively. Another suitable antimicrobial agent is a combination of DMDM hydantoin and iodopropynyl butylcarbamate, which is commercially available from Lonza Inc. as Glydant Plus. Other antimicrobial agents include quaternium-15, methyl paraben, ethyl paraben, propyl paraben, DMDM hydantoin, Suttocide A and the like. Another suitable antimicrobial agent is 1-BROMO-1-(BROMOMETHYL)-1,3-PROPANEDI-CARBONITRILE available under the name Tektamer. According to certain embodiments, the antimicrobial agent is present in the emulsion composition in amounts of from about 0.1%, 0.15%, 0.18% to about 0.2%, 0.25%, or 0.3% with from about 0.01%, 0.015, 0.025, 0.03% to 0.075,%, 0.1%, or 0.15% of the biocide active, present in the composition. The level of commercial antimicrobial biocide 'as-is' will vary dependent upon the concentration/activity of specific antimicrobial.

Optional Emulsion Composition Ingredients

According to the present disclosure, the emulsion compositions may optionally contain one or more optional ingredients. Examples of these ingredients include, but are not limited to: aesthetic components, pigments, colorings, chlorants, anti-caking agents, antifoaming agents, preservative, dye, antioxidants, fluorescence agents, binders, fumed silica, biological additives, buffering agents, bulking agents, chelating agents, chemical additives, solvents (other than water), cosmetic biocides, denaturants, humectants, opacifying agents, pH adjusters, process aids, reducing agents, sequestrants, binders, hydrocolloids, zeolites, and the like.

Optional ingredients, when present, are each typically employed in the compositions at levels of from about 0.0001%, 0.001%, or 0.01% to about 95%, 97%, 98%, or 99.5%, by weight of the emulsion composition.

Absorbent Article

According to the present disclosure, absorbent articles comprise the stable emulsion composition described above. In particular, the composition may be applied to one or more substrate surfaces of the article. For perspective, the articles of the present invention may comprise a topsheet having a garment facing surface and a body facing surface, a backsheet having a garment facing surface and a body facing surface, and an absorbent core disposed between said body facing surface of the backsheet and the garment facing surface of the topsheet.

In certain embodiments, the absorbent articles may take the form of a diaper, a pant product, an adult incontinence product, or a feminine hygiene product, e.g., a sanitary napkin or panty liner. Given these various product forms, additional components may also exist within the disposable absorbent article. Such components may be selected from the group consisting of an outer cover, side panels, a cuff, an elastic feature, a wing, a fastening system, and combinations thereof.

As used herein, the term "pant" refers to disposable garments having a waist opening and leg openings designed for infant or adult wearers. A pant may be placed in position on the wearer by inserting the wearer's legs into the leg openings and sliding the pant into position about the wearer's lower torso. A pant may be preformed by any suitable technique including, but not limited to, joining together portions of the article using refastenable and/or non-refastenable bonds (e.g., seam, weld, adhesive, cohesive bond, fastener, etc.). While the term "pant" is used herein, pants are also commonly referred to as "closed diapers", "prefastened diapers", "pull-on diapers", "training pants" and "diaper-pants". Suitable pants are disclosed in U.S. Pat. Nos. 5,246,433; 5,569,234, 6,120,487, 6,120,489, 4,940,464, 5,092,861, 5,897,545, 5,957,908, U.S. Patent Publication 2003/0233082A1, U.S. Pat. Nos. 3,860,003, 4,636,207, 4,695,278, 4,704,115, 4,795,454, 4,900,317, 4,909,803 (Reissued as USRE34920), 5,085,654, 5,492,751, 6,476,288, 6,627,787, 5,507,760, 5,609,587, 5,635,191, 5,643,588; 6,118,041, SIR H1630, U.S. Pat. Nos. 5,246,433, 5,769,838, 5,899,895, 5,899,896, and 6,120,487.

While the topsheet, the backsheet, and the absorbent core may be assembled in a variety of well known configurations, preferred diaper configurations are described generally in U.S. Pat. No. 3,860,003; U.S. Pat. No. 5,151,092; and U.S. Pat. No. 5,221,274; U.S. Pat. No. 5,554,145; U.S. Pat. No. 5,569,234; U.S. Pat. No. 5,580,411; and U.S. Pat. No. 6,004,306.

Topsheet

According to the present disclosure, absorbent articles may comprise a topsheet. The topsheet is preferably compliant, soft feeling, and non-irritating to the wearer's skin. It can be elastically stretchable in one or two directions. Further, the topsheet is liquid pervious, permitting liquids (e.g., menses, urine, and/or runny feces) to readily penetrate through its thickness. A suitable topsheet can be manufactured from a wide range of materials such as woven and nonwoven materials; apertured or hydroformed thermoplastic films; porous foams; reticulated foams; reticulated thermoplastic films; and thermoplastic scrims. Suitable woven and nonwoven materials may comprise of natural fibers such as wood or cotton fibers; synthetic fibers such as polyester, polypropylene, or polyethylene fibers; or combinations thereof. If the topsheet includes fibers, the fibers may be spunbond, carded, wet-laid, meltblown, hydroentangled, or otherwise processed as is known in the art. One suitable topsheet comprising a web of staple-length polypropylene fibers is manufactured by Veratec, Inc., a Division of International Paper Company, of Walpole, Mass. under the designation P-8.

In one embodiment, suitable topsheets are selected from high loft nonwoven topsheets and apertured film topsheet. Apertured film topsheet typically are pervious to bodily exudates, yet non-absorbent, and have a reduced tendency to allow fluids to pass back through and rewet the wearer's skin. Suitable apertured films include those described in U.S. Pat. Nos. 5,628,097, 5,916,661, 6,545,197, 6,107,539, and PCT Patent Publication WO 00/69382 A2.

Further, suitable topsheet materials for depositing solid excretions thereon may include nonwovens having apertures, which are at least in the portions that are aligned with the feces deposition region of the article. Suitable apertured nonwovens are described in more detail in U.S. Pat. Nos. 6,414,215, 5,342,338, and 5941864 and U.S. Patent Publication 2002/017376. In another embodiment of feces handling articles, such topsheets can be combined with feces handling members, for example, underlying such topsheets, and which are further described in the abovementioned patent documents.

Suitable formed film topsheets are described in U.S. Pat. Nos. 3,929,135, 4,324,246, 4,342,314, 4,463,045, 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T."

In certain embodiments, at least a portion of the topsheet is made of a hydrophobic material or is treated to be hydrophobic in order to isolate the wearer's skin from liquids contained in the absorbent core. If the topsheet is made of a hydrophobic material, preferably at least a portion of the upper surface of the topsheet is treated to be hydrophilic so that liquids will transfer through the topsheet more rapidly. The topsheet can be rendered hydrophilic by treating it with a surfactant or by incorporating a surfactant into the topsheet. Suitable methods for treating the topsheet with a surfactant include spraying the topsheet material with the surfactant and/or immersing the material into the surfactant. A more detailed discussion of such a treatment and hydrophilicity is contained in U.S. Pat. Nos. 4,988,344, 4,988,345, and 4950254. A more detailed discussion of some suitable methods for incorporating a surfactant in the topsheet 24 can be found in U.S. Statutory Invention Registration No. H1670. Alternatively, the topsheet may include an apertured web or film which is hydrophobic. This may be accomplished by eliminating the hydrophilizing treatment step from the production process and/or applying a hydrophobic treatment to the topsheet, such as a polytetrafluoroethylene compound like SCOTCHGUARD or a hydrophobic lotion composition, as described below. In such embodiments, it is preferred that the apertures be large enough to allow the penetration of aqueous fluids like urine without significant resistance.

Any portion of the topsheet may be coated with a lotion as is known in the art. Examples of suitable lotions include those described in U.S. Pat. Nos. 5,607,760, 5,609,587, 5,635,191, 5,643,588, and 5,968,025. The lotion may function alone or in combination with another agent as the hydrophobizing treatment described above. The topsheet may also include or be treated with antibacterial agents, some examples of which are disclosed in PCT Publication No. WO 95/24173. Further, the topsheet, the outer cover or any portion of the topsheet or outer cover may be embossed and/or matte finished to provide a more cloth like appearance.

The topsheet may comprise one or more apertures to ease penetration of exudates therethrough, such as urine and/or feces (solid, semi-solid, or liquid). The size of at least the primary aperture is important in achieving the desired waste encapsulation performance. If the primary aperture is too small, the waste may not pass through the aperture, either due to poor alignment of the waste source and the aperture location or due to fecal masses having a diameter greater than the aperture. If the aperture is too large, the area of skin that may be contaminated by "rewet" (from the article) is increased. Typically, the aperture should have an area of between about 10 cm$^2$ and about 50 cm$^2$. In another embodiment, the aperture has an area of between about 15 cm$^2$ and 35 cm$^2$.

Further, the topsheet may be fully or partially elasticated or may be foreshortened so as to provide a void space between the topsheet and the core. Exemplary structures including elasticized or foreshortened topsheets are described in more detail in U.S. Pat. Nos. 4,892,536, 4,990,147, 5,037,416, and 5,269,775.

Backsheet

The backsheet may be impervious to fluids (e.g., menses, urine, and/or runny feces) and may be manufactured from a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, and/or composite materials such as a film-coated nonwoven material (i.e., having an inner film layer and an outer nonwoven layer). A suitable backsheet is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet may be embossed and/or matte-finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent a garment-facing surface and a body facing surface, respectively, of the absorbent core. The absorbent core may be joined with the topsheet, the backsheet, or both in any manner as is known by attachment means such as those well known in the art. However, embodiments of the present disclosure are envisioned wherein portions of the entire absorbent core are unattached to one or both of the topsheet and the backsheet.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258, HL-1358, or HL-2031. The attachment means may comprise an open pattern network of filaments of adhesive as is disclosed in U.S. Pat. No. 4,573,986. An exemplary attachment means of an open pattern network of filaments comprises several lines of adhesive filaments swirled into a spiral pattern such as illustrated by the apparatus and method shown in U.S. Pat. Nos. 3,911,173, 4,785,996 and 4,842,666. Alternatively, the attachment means may comprise heat bonds, pressure bonds, ultrasonic bonds, dynamic mechanical bonds, or any other suitable attachment means or combinations of these attachment means as are known in the art.

The backsheet may include an inner and outer layer, each of which can be bonded to the other by a variety of means known in the art, including thermal bonds, adhesive bonds, ultrasonic lamination, or the like. Intimate bonding of the inner and outer layers in the vicinity of the graphic reduces light diffraction and thus improves the brightness and overall visibility of graphic. Adhesive bonding can also be accomplished using adhesive slot coating, high frequency oscillation patterns, for example in swirl or spray patterns, and other fine denier and/or high coverage application techniques. Suitable laminate adhesives, which can be applied continuously or intermittently, can be obtained from Findley Adhesives, Inc. or from National Starch and Chemical Company.

The outer layer of the backsheet can be made in a variety of forms using different processes. For example, the outer layer may be formed as a carded web, a bonded carded web, a spunbond web, a needled fabric, a woven fabric, or the like to provide a generally cloth-like texture to the wearer. Other additives such as titanium dioxide can represent about 0.5% or less, particularly about 0.3% or less, of the outer layer. In one particular embodiment, the outer layer comprises a spunbond web formed of about 99.5 to 100% polypropylene resin and about 0.5% or less other additives. The outer layer is desirably a lightweight material having a basis weight of from about 15 to about 30 gsm and in another embodiment from about 15 to about 25 gsm.

Absorbent Core

The articles of the present disclosure may additionally comprise one or more absorbent cores. The absorbent core is at least partially disposed between the topsheet and the backsheet and may take on any size or shape that is compatible with the disposable absorbent article. Exemplary absorbent structures for use as the absorbent core of the present invention that have achieved wide acceptance and commercial success are described in U.S. Pat. Nos. 4,610,678, 4,673,402, 4,888,231, and 4,834,735. The absorbent core may further comprise the dual core system containing an acquisition/distribution core of chemically stiffened fibers positioned over an absorbent storage core as detailed in U.S. Pat. Nos. 5,234,423 and 5,147,345.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (for example, rectangular, oval, hourglass, "T" shaped, dog bone, asymmetric, etc.).

The absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these.

As discussed herein "absorbent gelling materials" and "superabsorbent polymers" are those materials that, upon contact with aqueous fluids, such as bodily fluids, imbibes such fluids and form hydrogels. These absorbent gelling materials are typically capable of absorbing large quantities of aqueous bodily fluids, and further capable of retaining such absorbed fluids under moderate pressures. These absorbent gelling materials are typically in the form of discrete, nonfibrous particles. Other forms, such as fibers, foams, sheets, strips, or other macrostructures, are also suitable for use herein. Suitable absorbent gelling materials in the form of open cell foams may include those disclosed in U.S. Pat. Nos. 3,563,243, 4,554,297, 4,740,520, and 5,260,345.

The configuration and construction of the absorbent core may also be varied (for example, the absorbent core may have varying caliper zones and/or have a profile so as to be thicker in the center; hydrophilic gradients; superabsorbent gradients; or lower average density and lower average basis weight zones, for example, acquisition zones; or may comprise one or more layers or structures). The total absorbent capacity of the absorbent core should, however, be compatible with the design loading and the intended use of the absorbent article. Further, the size and absorbent capacity of the absorbent core may be varied to accommodate different uses such as diapers, incontinence pads, pantiliners, regular sanitary napkins, and overnight sanitary napkins, and to accommodate wearers ranging from infants to adults. The absorbent core can include other absorbent components that are often used in absorbent articles, for example, a dusting layer, a wicking or acquisition layer, or a secondary topsheet for increasing the wearer's comfort.

In certain embodiments of the present disclosure, the absorbent article may also include a sublayer disposed between the topsheet and the backsheet. The sublayer may have a body facing surface and a garment facing surface and may be any material or structure capable of accepting, storing or immobilizing bodily exudates. Thus, the sublayer may include a single material or a number of materials operatively associated with each other. Further, the sublayer may be integral with another element of the absorbent article or may be one or more separate elements joined directly or indirectly with one or more elements of the article. Further, the sublayer may include a structure that is separate from the core or may include or be part of at least a portion of the core.

Suitable materials for use as the sublayer may include large cell open foams, macro-porous compression resistant nonwoven highlofts, large size particulate forms of open and closed cell foams (macro and/or microporous), highloft nonwovens, polyolefin, polystyrene, polyurethane foams or particles, structures comprising a multiplicity of vertically oriented looped strands of fibers, absorbent core structures described above having punched holes or depressions, and the like. One embodiment of a sublayer includes a mechanical fastening loop landing element, having an uncompressed thickness of about 1.5 millimeters available as XPL-7124 from the 3M Corporation of Minneapolis, Minn. Another embodiment includes a 6 denier, crimped and resin-bonded nonwoven highloft having a basis weight of 110 grams per square meter and an uncompressed thickness of 7.9 millimeters which is available from the Glit Company of Wrens, Ga. Other suitable absorbent and nonabsorbent sublayers are described in U.S. Pat. Nos. 6,680,422 and 5,941,864. Further, the sublayer, or any portion thereof, may include or be coated with a lotion or other known substances to add, enhance or change the performance or other characteristics of the element.

Additionally, suitable absorbent cores may contain reduced amounts of cellulosic airfelt material. For instance, such cores may comprise less than about 40%, 30%, 20%, 10%, 5%, or even 1%. Such a core comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335, 5,562, 646, 5,669,894, 6,790,798, US Patent Publications 2004/0158212A1, 2004/0097895A1, U.S. application Ser. Nos. 10/758,375, and 10/758,138, both filed on Jan. 15, 2004.

In further embodiments, the articles according to the present disclosure may further comprise a wetness sensation member. This member may be disposed in various locations within the article. For instance, the wetness sensation member may be disposed on the topsheet. The member may comprise a permeable layer and an impermeable layer, wherein urine passes through the permeable layer and not through the impermeable layer such that a wearer is made of aware of the fact that urination has occurred as a result of the "wet" feeling. Suitable members are detailed in U.S. Pat. No. 6,627,786.

Emulsion Composition Application

The film that is formed from the oil-in-water emulsion composition according to the present disclosure is manufactured by combining the components as described above. The mixture of components is mixed at high shear using approximately 8-10 passes through an IKA rotor-stator mixer (for example, IKA DR2000/4, model P007528 with 3 sets of superfine rotor/stator) to yield a pseudoplastic (for example, shear thinning) composition. This resultant emulsion composition remains "stable", i.e., such that the emulsion droplets do not agglomerate to droplets having a median droplet size of greater than about 1 μm (or less than about 0.8 μm or even less than about 0.7 μm) over a time period of at least about one month, three months, six months, nine months, or even about one year. This "stable" character of the emulsion composition prior to application to a substrate or disposable absorbent article facilitates long term storage and transport of the materials in preparation for final product manufacture. Retaining a 'stable' median droplet size smaller than about 1 μm or in another embodiment less than about 0.8 μm or in yet another embodiment less than about 0.7 μm, is desirable, as larger perfume oil droplets, lead to rapid perfume loss from the resultant (dried) film-residue, overtime, following dehydration of the emulsion Once the emulsion composition is stored and shipped to the product manufacturer, it typically applied to one or more substrate surfaces of a disposable absorbent article via a suitable applicator. Suitable applicators include, but not limited to, one or more bead extruders, slot die coaters, spray nozzles, and combinations thereof. The applicator system may comprise one or more of these applicators, which may be arranged parallel across the width of the web, or arranged in series. In any event, whichever applicator is selected, it must be capable of applying a liquid containing suspended particles on to a substrate which may be moving.

In one embodiment, the composition is sprayed onto a substrate, for example, a fibrous sublayer of a disposable absorbent article, such that a film is formed upon drying. Typically, the spray mode may be selected from an intermittent spray mode, constant spray mode, or a fluid stream mode.

No matter what application method is used, a film of a continuous or discontinuous nature will be formed from emulsion droplets having a median droplet size of less than about 1 μm. As used herein, "discontinuous" means interrupted with spaces void of dried emulsion composition over an entire substrate surface. As used herein, "continuous" means uninterrupted with spaces void of dried emulsion composition over an entire substrate surface. This technique of applying such a composition to a substrate's surface is also known in the industry as "plating". Therefore, the film that is formed may also be referred to as a plate once the composition has dried on the substrate surface. It should be noted that a continuous film or plate according to the present disclosure may ultimately become a discontinuous film due to handling or manufacture of the end absorbent article.

Typically, the emulsion composition is applied to the substrate at a rate effective for high speed final product manufacture with desired perfume level. The rate at which the emulsion composition is delivered to a substrate or disposable article will depend upon many factors, such as but not limited to, the composition of the substrate, nature of the emulsion composition, amount of emulsion composition desired on substrate (for example, grams of emulsion composition per square meter of substrate), applicator type, and combinations thereof.

In one embodiment, the emulsion composition is applied to a substrate or one or more surfaces of a disposable absorbent article at a rate of from about 1 to about 500 grams of composition per minute. In certain embodiments, the emulsion composition is applied such that there is perfume add-on to each substrate or surface of the absorbent article of at least about 15 mg, 20 mg, 25 mg, 30 mg, 35 mg, 40 mg, 45 mg or even at least about 50 mg.

EXAMPLES

The following examples are given solely for the purposes of illustration and are not to be construed as limitations of the present disclosure.

Examples I-II

Emulsion compositions according to the present disclosure are made by mixing the following ingredients at high shear.

| Ingredients (wt %) | Example I | Example II |
|---|---|---|
| Water | 51.76 | 49.02 |
| Modified Starch National LNP GLUK 2004 | 26.0 | 24.6 |
| Perfume (Quest Q31535) | 21.0 | 25.0 |
| Surfactant (sorbitan monolaurate) | 0.85 | 1.00 |
| Rheology Modifier (xanthan gum) | 0.2 | 0.2 |
| Antimicrobial agent (Kathon CG) | 0.19 (0.039 biocide active) | 0.18 (0.037 biocide active) |
| Median droplet sizes | | |
| Median droplet size (μm) immediately after mixing | 0.460 | 0.387 |
| Median droplet size (μm) after 3 months and at ambient temperature | 0.561 | 0.509 |

Examples III-IV

Disposable absorbent articles according to the present disclosure that are diapers, training pants, or adult incontinence products are made as detailed in any one of U.S. Pat. Nos. 3,860,003, 4,636,207, 4,695,278, 4,704,115, 4,795,454, 4,900,317, 4,909,803 (Reissued as USRE34920), 5,085,654, 5,492,751, 6,476,288, 6,627,787, 5,507,760, 5,609,587, 5,635,191, 5,643,588, 6,118,041, SIR H1630, U.S. Pat. Nos. 5,246,433, 5,769,838, 5,899,895, 5,899,896, and 6,120,487 by spraying the emulsion compositions of Examples I or II onto the garment facing surface of a fibrous sublayer. This sublayer is situated between a topsheet and an absorbent core and the sublayer and core are sandwiched between the topsheet and a backsheet. The emulsion composition is sprayed or applied in a stream onto the garment facing surface to provide a perfume add-on amount of from about 20 mg to about 50 mg. The sprayed composition is allowed to dry until a discontinuous film is formed.

Examples V-X

The following Examples V-X are prepared using the following: 1) tank vessel, ~50 Kg capacity; 2) overhead mixer; 3) transfer pump; 4) high shear mixer, for example, IKA DR2000/4 model P007528; and 5) heat exchanger.

Premixes of oil phase, and thickener blend are pre-made prior to final batch making.

Thickener Blend

Rheology modifier is pre-blended with some fractional level of co-surfactant material, heating if necessary to liquefy the co-surfactant material, and stirring the powder rheology modifier into liquid co-surfactant, by hand, to make a thick paste. Seal for later, future use, within 7 days typically.

Oil Phase Premix

Oil phase of perfume+co-surfactant, at 20° C.-25° C., are blended together and hand-stirred with large spatula to mix, to produce an oil phase premix. In one embodiment, premix to be sealed/stored for later, future use.

Starch Solution

Comprised of modified starch and water and antimicrobial, is prepared, if needed, optionally prepared in advance, separately, to a concentration solids level appropriate to specific modified-starch selected, with a maximum solids content equal to the solubility limit of specific modified-starch in water at 20° C.

Examples V-VI

The following Examples V and VI illustrate formulations that can be used as oil-in-water emulsion compositions according to the present disclosure.

Example V

| INCI | TRADE NAME | % w/w (g) |
|---|---|---|
| Aqua | Water | QS |
| Modified Food starch | National LNP GLUK 2004 | 25 |
| Essential Oil | Perfume Symrise AC11881 | 15 |
|  | Tektamer | 0.0007 (7 ppm) |

Example V was prepared according to the following procedure. A tank vessel is filled with 7500 g National GLUK 2004 modified starch (33% active), at room temperature, approximately 23° C. 1000 g of water is then added, agitation is started, and maintained at 125 rpm, for 10 minutes. Next, 1500 g Symrise AC11881 perfume is added to the vessel and stirred at 160 rpm, for 15 minutes. Next, the transfer pump and high shear mill are started, routing through heat exchanger, and recirculating back to tank vessel. (flow rate ~1658 g/min, mill set @3545 rpm, heat exchanger=0.9 Kg/min 9° C. cooling water flow, batch temperature is 18.5° C.). At approximately 6 minute interval (1 complete) sample composition, and identify as 'X' cycles and time. Continue until 5×, complete cycles were passed (approximately 30 minutes total). Collect composition in clean plastic pails and seal.

Example VI

| INCI | TRADE NAME | % w/w (g) |
|---|---|---|
| Aqua | Water | QS |
| Modifed Food starch | National LNP GLUK 2004 | 25 |
| Essential Oil | Perfume Symrise AC11881 | 15 |
| Sorbitan monolaurate | Glycomul L | 0.60 |
| Xanthan gum | Kelzan ASX | 0.25 |
|  | Tektamer | 0.0007 (7 ppm) |

Example VI was prepared according to the following procedure. A thickener blend is prepared by combining 75 g of rheology modifier (Kelzan ASX) and 150 g of co-surfactant (Glycomul L) in a plastic jar, stir by hand vigorously. The thickener is sealed and allowed to stand for approximately 2 hours, at room temp. Next, an Oil Phase Premix is prepared by combining 1515 g Symmrise AC 11881 perfume and 10.1 g co-surfactant (Glycomul L) in a 2 gallon plastic pail. The premix is sealed and allowed to stand for approximately 20 minutes. Next, a tank vessel is filled with 7500 g National GLUK 2004 modified starch (33%), at room temperature, approximately 23° C. Next, 915 g water is added, agitation is started and maintained at 135 rpm, for 5 minutes. Next, 75 g of thickener blend is added, agitation is started and maintained at 200 rpm, for 10 minutes. Next, 1510 g Oil Phase Premix is added to the vessel and stirred at 200 rpm, for 15 minutes. The pump and high shear mill are started, routing through heat exchanger, and recirculating back to tank vessel. (flow rate ~2254 g/min, mill set @3545 rpm, heat exchanger=0.9 Kg/min @9C cooling water flow, batch temperature is 22° C.). At approximately 4.5 minute interval (1 complete) sample composition, and ID as 'X' cycle & time. Continue until 5×, complete cycles were passed (approximately 25 minutes total). Collect composition in clean plastic pails and seal.

TABLE I

Visual Observations of Phase Separation

| Composition | Phase Separation | |
|---|---|---|
|  | @ 2 day | @ 4 wk |
| V-5X | No | YES (~11% clear layer) |
| VI-5X | No | No |

Observational data (measuring layer of separation relative to total height of composition in a eight dram vial) illustrates that Example V experiences phase separation after four weeks while Example VI which includes a co-surfactant and rheology modifier does not. This demonstrates the stability of oil-in-water emulsion compositions including co-surfactants and rheology modifiers.

Examples VII-X

The following Examples VII-X illustrate formulations that can be used as oil-in-water emulsion compositions according to the present disclosure.

Example VII

| INCI | TRADE NAME | % w/w (g) |
|---|---|---|
| Aqua | Water | QS |
| Modifed Food starch | National LNP GLUK 2004 | 22.9 |
| Essential Oil Perfume | Quest 31535 | 30 |
|  | Tektamer | 0.0007 (7 ppm) |

Example VII was prepared according to the following procedure. A tank vessel is filled with 6865 g National GLUK 2004 modified starch (33% active), at room temperature, approximately 23° C. 135 g of water is then added, agitation is started, and maintained at 135 rpm, for 10 minutes. Next, 3000 g Quest Q31535 perfume is added to the vessel and stirred at 210 rpm, for 15 minutes. Next, the transfer pump and high shear mill are started, routing through heat exchanger, and recirculating back to tank vessel. (flow rate ~800 g/min, mill set @3545 rpm, heat exchanger=0.9 Kg/min @ 9° C. cooling water flow, batch temperature is 23° C.). At approximately 12.5 minute interval (1 complete) sample composition, and identify as 'X' cycles & time. Continue until 5x, complete cycles were passed (approximately 62 minutes total). Collect composition in clean plastic pails and seal.

Example VIII

| INCI | TRADE NAME | % w/w (g) |
|---|---|---|
| Aqua | Water | QS |
| Modifed Food starch | National LNP GLUK 2004 | 22.9 |
| Essential Oil | Perfume Quest 31535 | 30 |
| Sorbitan monolaurate | Glycomul L | 1.2 |
| | Tektamer | 0.0007 (7 ppm) |

Example VIII was prepared according to the following procedure. An Oil Phase Premix is prepared by combining 3060 g Quest Q31535 perfume and 102 g co-surfactant (Glycomul L) in a 5 gallon plastic pail and stirring with large spatual. The premix is sealed and allowed to stand for approximately 20 minutes. Next, a tank vessel is filled with 6864 g National GLUK 2004 modified starch (33% active), at room temperature, approximately 23° C., agitation is started and maintained at 150 rpm and maintained throughout batch making process. Next, 16 g water is added and 20 g of co-surfactant (Glycomul L). Next the Oil Phase Premix is added and stirred at 220 rpm for 15 minutes. The pump and high shear mill are started, routing through heat exchanger, and recirculating back to tank vessel. (flow rate ~1230 g/min, mill set @3545 rpm, heat exchanger=1.9 Kg/min @ 9C cooling water flow, batch temperature is 22° C.). At approximately 8 minute interval (1 complete) sample composition, and ID as 'X' cycle & time. Continue until 5x, complete cycles were passed (approximately 40 minutes total). Collect composition in clean plastic pails and seal.

Example IX

| INCI | TRADE NAME | % w/w (g) |
|---|---|---|
| Aqua | Water | QS |
| Modifed Food starch | National LNP CLUK 2004 | 22.9 |
| Essential Oil | Perfume Quest 31535 | 30 |
| Xanthan gum | Kelzan ASX | 0.15 |
| | Kathon CG | 0.0001 (1 ppm) |
| | Tektamer | 0.0007 (7 ppm) |

Example IX was prepared according to the following procedure. A thickener blend is prepared by combining 16 g of rheology modifier (Kelzan ASX), 128 g water, 533 g of National GLUK 2004 modified starch (33% active) and 0.1 g Kathon CG in 1 L plastic bottle. The thickener is sealed and allowed to stand for approximately 24 hours, at room temp. Next, a tank vessel is filled with 6364 g National GLUK 2004 modified starch (33%), at room temperature ~23C, start agitation at 150 rpm, and maintained through out batch-making process. Add 636 g Thickener blend, stir at 300 rpm, 10 minutes. Add 3000 g of Quest Q31535 perfume to vessel, stir at 220 rpm, for 15 minutes. Start pump+high shear mill, routing through heat exchanger, and recirculating back to tank vessel. (flow rate ~1910 g/min, mill set @3545 rpm, heat exchanger=1.9 Kg/min @ 9C cooling water flow). At approximately 5 min interval (1 complete) sample composition, and ID as 'X' cycle & time. Continue until 5x, complete cycles were passed approximately 30 minutes total. Collect composition in clean plastic pails, seal.

Example X

| INCI | TRADE NAME | % w/w (g) |
|---|---|---|
| Aqua | Water | QS |
| Modified Food starch | National LNP CLUK 2004 | 22.9 |
| Essential Oil | Perfume Quest 31535 | 30 |
| Sorbitan monolaurate | Glycomul L | 1.2 |
| Xanthan gum | Kelzan ASX | 0.15 |
| | Kathon CG | 0.0015 (15 ppm) |

Example X was prepared according to the following procedure. Prepare Thickener Blend: Combine 75 g Kelzan ASX+ 150 g Glycomul L, in plastic jar, stir by hand vigorously. Seal and allow to stand approximately 2 hours, at room temp. Prepare Oil Phase Premix Combine 3106.8 g Quest 31535 perfume+93.2 g Glycomul L, in 5 gal. plastic pail, stir with large spatula, allow to stand 20 minutes. Fill tank vessel with 6865 g National GLUK 2004 modified starch (33% active), at room temperature approximately 23C, start agitation at 150 rpm, and maintained through out batch-making process. Add 45 g Thickener blend, stir at 200 rpm, 10 minutes. Add 3090 g of oil premix with Quest Q31535 perfume to vessel, stir at 220 rpm, for 15 minutes. Start pump+high shear mill, routing through heat exchanger, and recirculating back to tank vessel. (flow rate ~2024 g/min, mill set @3545 rpm, heat exchanger=1.9 Kg/min @ 9C cooling water flow). At approximately 5 minute interval (1 complete) sample composition, and ID as 'X' cycle & time. Continue until 5x, complete cycles were passed approximately 30 minutes total. Collect composition in clean plastic pails, seal.

TABLE II

Median Particle size stability (nanometer)

| Composition | initial | @ 20 d 25 C. | @ 50 d 25 C. |
|---|---|---|---|
| VII-1X process cycle | 597 | 1282 | 1306 |
| VII-5X process cycle | 432 | 1687 | 1690 |
| VIII-1X process cycle | 463 | 598 | 664 |
| VIII-5X process cycle | 365 | 546 | 892 |
| IX-1X process cycle | 913 | 1123 | 1124 |
| IX-5X process cycle | 631 | 880 | 809 |
| X-1X process cycle | 623 | 1090 | 883 |
| X-5X process cycle | 581 | 729 | 634 |

Particle size data comparison illustrates the rapid change/instability of particle size growth of Example VII without either co-surfactant or rheology modifier inclusion, and the benefit of adding, principally, the co-surfactant in reducing and slowing the perfume oil phase median droplet size, for example, Example VIII and concurrently, the added difficulty to particle reduction with rheology modifier added, for example, Example IX. Example X with both co-surfactant and rheology modifier, and several process cycles, for example, 5x, yields a median particle size below 1000 nanometers (1 micron) with sufficient viscosity to resist composition phase separation upon standing and storage. Examples VIII, 1x and X illustrate the flexibility to tailor composition particle size, and viscosity, produced initially, and upon standing/storage, by use of process conditionscycles, and the modified starch, co-surfactant and rheology modifier, to form stable oil-in-water emulsions.

Film-Residue: Perfume Retention Upon Drying of Aqueous Composition

Approximately 0.12 g of compositions of Examples VII-X, were weighed to 5 places onto a dry, clean Bounty™ towel section of ~1"×3" in size and allowed to dry overnight, uncovered and open to ambient environment. A solvent extract of the residue was made after 24 hrs 'drying' the compositions, and a measure of the perfume amount in the residue quantified. Samples were collected in duplicate, and results averaged, for each time_x_condition assessment.

TABLE III

Perfume Retention Upon Drying of Aqueous composition

| Composition | % Perfume Retained | | |
|---|---|---|---|
| | @ 24 hr | @ 2 wk | @ 4 wk |
| VII-1X @ 2 d age | 84.7 | 71.0 | 60.4 |
| VII-5X @ 2 d age | 88.4 | 76.7 | 68.4 |
| VIII-1X @ 2 d age | 81.4 | 77.2 | 65.8 |
| VIII-5X @ 2 d age | 88.1 | 78.4 | 65.4 |
| IX-1X @ 2 d age | 81.7 | 76.9 | 65.0 |
| IX-5X @ 2 d age | 85.0 | 81.2 | 71.5 |
| X-1X @ 2 d age | 84.9 | 75.2 | 68.7 |
| X-5X @ 2 d age | 87.1 | 78.4 | 70.4 |
| VII-1X @ 16 d age | 89.2 | 61.6 | |
| VII-5X @ 16 d age | 86.1 | 63.7 | |
| VIII-1X @ 16 d age | 93.7 | 63.3 | |
| VIII191-5X @ 16 d age | 91.1 | 71.0 | |
| IX-1X @ 16 d age | 85.2 | 71.9 | |
| IX-5X @ 16 d age | 90.5 | 46.8 | |
| X-1X @ 16 d age | 84.2 | 69.7 | |
| X-5X @ 16 d age | 87.1 | 75.4 | |
| VII-5X @ 35 d age | 89.6 | | |
| VIII-5X @ 35 d age | 93.2 | | |
| IX-5X @ 35 d age | 92.6 | | |
| X-5X @ 35 d age | 94.5 | | |
| Q31535 perfume | 29.8 | <2.0 | |

Particle size of the oil phase/perfume droplet in the aqueous emulsion and, upon drying, in the resultant odor-controlling film, is a primary factor to rate of perfume loss (retention) from dried odor-controlling film. Much of the perfume loss was skewed to the more volatile perfume components. The data illustrates the benefit of adding either or both co-surfactant and rheology, modifier, for reducing the perfume loss, from the resultant dried odor-controlling film, with the advantage growing over time of standing/storage.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   a topsheet;
   a backsheet;
   an absorbent core disposed between the topsheet and the backsheet;
   a fibrous sublayer situated between the topsheet and the backsheet, and having a garment-facing surface;
   a starch encapsulated perfume accord in the form of a dried film residue of a stable oil-in-water emulsion composition applied to the absorbent article, the emulsion composition comprising:
      a) an aqueous phase comprising a modified starch having a hydrophobic group, and water;
      b) an oil phase comprising a perfume;
      c) an effective amount of a rheology modifier;
      d) an effective amount of a co-surfactant; and
      e) an effective amount of an antimicrobial agent; and
   optionally, a lotion disposed on any portion of the topsheet;
   wherein the starch encapsulated perfume accord is disposed on the garment-facing surface of the fibrous sublayer.

2. The absorbent article of claim 1 wherein said modified starch is an OSAN-substituted starch.

3. The absorbent article of claim 2 wherein said modified starch is a hydrolyzed starch.

4. The absorbent article of claim 1 wherein said co-surfactant exhibits an HLB of from about 8 to about 10.

5. The absorbent article of claim 1 wherein said co-surfactant is a sorbitan fatty ester.

6. The absorbent article of claim 1 wherein said rheology modifier is an aqueous phase rheology modifier.

7. The absorbent article of claim 1 wherein said composition comprises oil phase droplets having a median size of less than about 0.8 μm.

8. The absorbent article of claim 1 wherein said article further comprises one or more additional substrate components selected from the group consisting of a topsheet, backsheet, absorbent core, sublayer, wicking layer, dusting layer, core cover, and combinations thereof.

9. A method of imparting malodor masking character to a disposable absorbent article having one or more layers, each layer having a garment-facing surface, said method comprising the steps of:
   a) providing a stable oil-in-water emulsion composition comprising:
      i) an aqueous phase comprising a modified starch having a hydrophobic group, and water;
      ii) an oil phase comprising a perfume;
      iii) an effective amount of a rheology modifier;
      iv) an effective amount of a co-surfactant; and
      v) an effective amount of an antimicrobial agent;
      wherein said emulsion composition contains oil phase droplets having a median size of less than about 1 μm;
   b) during manufacture of the article, disposing on at least one of the one or more garment-facing surfaces an effective amount of the stable emulsion composition; and
   c) drying the stable oil-in-water emulsion to form a starch encapsulated perfume accord in the form of a dried film residue on at least one of the one or more garment-facing surfaces.

10. An absorbent article comprising:
    a topsheet;
    a backsheet;

an absorbent core disposed between the topsheet and the backsheet;

a fibrous sublayer situated between the topsheet and the backsheet, and having a garment-facing surface;

a starch encapsulated perfume accord in the form of a dried film residue of a stable oil-in-water emulsion composition applied to the absorbent article, the emulsion composition comprising:

a) an aqueous phase comprising modified starch and water;
  b) an oil phase comprising a perfume;
  c) an effective amount of an aqueous phase rheology modifier;
  d) an effective amount of a co-surfactant; and
  e) an effective amount of an antimicrobial agent; and optionally, a lotion disposed on any portion of the topsheet;

wherein said emulsion composition contains oil phase droplets having a median size of less than about 1 μm and the starch encapsulated perfume accord is disposed on the garment-facing surface of the fibrous sublayer.

11. The article of claim 10 wherein the rheology modifier is selected from the group consisting of polysaccharides, maltodextrins, natural gums, Xanthan gum, Gellan gum, Diutan gum, Welan gum, Gum Arabic, Guar gum, hydroxyl propyl distarch phosphate, and starch octenyl succinate (undegraded).

12. The article of claim 10 wherein the rheology modifier is a pseudoplastic material.

13. An absorbent article comprising:

a topsheet;

a backsheet;

an absorbent core disposed between the topsheet and the backsheet;

a fibrous sublayer situated between the topsheet and the backsheet, and having a garment-facing surface;

a starch encapsulated perfume accord in the form of a dried film residue of a stable oil-in-water emulsion composition applied to the absorbent article, the emulsion composition comprising:

a) an aqueous phase comprising modified starch and water;
  b) a perfume containing less than 15% by weight components that have an octanol-water partition coefficient (P)<1;
  c) an effective amount of a rheology modifier;
  d) an effective amount of a co-surfactant; and
  e) an effective amount of an antimicrobial agent;

wherein said emulsion composition contains oil phase droplets having a median size of less than about 1 μm and the starch encapsulated perfume accord is disposed on the garment-facing surface of the fibrous sublayer.

* * * * *